United States Patent [19]
Hansenne

[11] Patent Number: 5,609,853
[45] Date of Patent: Mar. 11, 1997

[54] PHOTOPROTECTIVE/COSMETIC COMPOSITIONS COMPRISING SYNERGISTIC ADMIXTURE OF SUNSCREEN COMPOUNDS

[75] Inventor: Isabelle Hansenne, Paris, France

[73] Assignee: L'Oreal, Paris, France

[21] Appl. No.: 464,940

[22] Filed: Jun. 5, 1995

[30] Foreign Application Priority Data

Jun. 3, 1994 [FR] France ................... 94 06829

[51] Int. Cl.$^6$ .................. A61K 7/42; A61K 7/40
[52] U.S. Cl. ............. 424/59; 424/60; 424/401; 514/844; 514/938
[58] Field of Search ............. 424/59, 60, 401; 514/938, 844

[56] References Cited

FOREIGN PATENT DOCUMENTS 0518772  12/1992  European Pat. Off. .
9111989  8/1991  WIPO .

OTHER PUBLICATIONS

Shaath, N., "Encyclopedia of UV Absorbers for Sunscreen Products", Cosmetics & Toiletries, vol. 102, Mar. 1987 pp. 21–36.

Rollants, R., et al, "A Survey of Ultraviolet Absorbers in Commercially Available Sun Products" International Journal of Dermatology, May 1983 vol. 22, pp. 247–255.

*Primary Examiner*—Shelley A. Dodson
*Attorney, Agent, or Firm*—Burns, Doane, Swecker & Mathis, L.L.P.

[57]  ABSTRACT

Topically applicable sunscreen/cosmetic compositions well suited for enhanced photoprotection of human skin and/or hair against the damaging effects of UV-A and UV-B irradiation, particularly solar radiation, comprise a photoprotecting synergistically effective amount of (i) benzene-1,4-di(3-methylidene-10-camphorsulfonic)acid, optionally either partially or totally neutralized, and (ii) 2-ethylhexyl α-cyano-β,β-diphenylacrylate, in a cosmetically acceptable vehicle, diluent or carrier therefor.

25 Claims, No Drawings

PHOTOPROTECTIVE/COSMETIC COMPOSITIONS COMPRISING SYNERGISTIC ADMIXTURE OF SUNSCREEN COMPOUNDS

CROSS-REFERENCE TO COMPANION APPLICATIONS

Copending applications Ser. No.
[Attorney Docket No. 016800-028], Ser. No. 08/463,221
[Attorney Docket No. 016800-029], Ser. No. 08/463,505
[Attorney Docket No. 016800-030], Ser. No. 08/463,503 U.S. Pat. No. 5,489,431
[Attorney Docket No. 016800-031], Ser. No. 08/463,762
[Attorney Docket No. 016800-032], Ser. No. 08/463,304
[Attorney Docket No. 016800-033], Ser. No. 08/463,508
[Attorney Docket No. 016800-034], Ser. No. 08/461,015
[Attorney Docket No. 016800-035], Ser. No. 08/463,507
each filed concurrently herewith and each assigned to the assignee hereof.

BACKGROUND OF THE INVENTION

1. Technical Field of the Invention

The present invention relates to novel cosmetic compositions for topical application, for the photoprotection of the skin and/or the hair against ultraviolet radiation (such compositions hereinafter simply designated "sunscreen," "sunscreen/cosmetic" or "photoprotective/sunscreen" compositions), and to the use of same for the cosmetic applications indicated above.

This invention more especially relates to the aforesaid sunscreen/cosmetic compositions comprising, in a cosmetically acceptable vehicle, carrier or diluent, combinatory immixture of at least two particular and unique sunscreen compounds, namely, on the one hand, benzene-1,4-di(3-methylidene-10-camphorsulfonic)acid and, on the other, 2-ethylhexyl α-cyano-β,β-diphenylacrylate. This admixture imparts enhanced solar protection factors to the subject compositions via an unexpected synergistic effect.

2. Description of the Prior Art

It is well known to this art that light radiation of wavelengths of from 280 nm to 400 nm promotes tanning of the human epidermis, and that irradiation of wavelengths of from 280 to 320 nm, i.e., UV-B irradiation, causes erythema and burning of the skin which can impair the development of a natural tan; hence, such UV-B radiation must thus be screened from the skin.

It is also known to this art that UV-A radiation, of wavelengths from 320 to 400 nm, which tans the skin, also adversely affects it, in particular in the event of sensitive skin or a skin which is continually exposed to solar radiation.

UV-A rays cause, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of cosmetic compositions intended for the photoprotection (UV-A and/or UV-B) of human skin are known to this art.

These photoprotective/sunscreen compositions are typically oil-in-water emulsions (namely, a cosmetically acceptable vehicle, carrier or diluent comprising an aqueous continuous dispersing phase and an oily discontinuous dispersed phase) which contains, in various concentrations, one or more standard lipophilic and/or hydrophilic organic sunscreen compounds capable of selectively absorbing harmful or deleterious UV radiation. These sunscreen compounds (and the amounts thereof) are selected as a function of the desired sun protection factor (the sun protection factor (SPF) being expressed mathematically by the ratio of the irradiation time required to attain the erythema-forming threshold with the UV screening agent to the time required to attain the erythema-forming threshold in the absence of UV screening agent).

SUMMARY OF THE INVENTION

It has now unexpectedly and surprisingly been determined that a unique combination of two particular sunscreen compounds, in proportions within well-defined limits, provides photoprotective/sunscreen compositions having protection factors which are markedly improved, and in all instances conspicuously superior to those which may be obtained, for an equal concentration of sunscreen compound and in a vehicle identical in nature, employing either of the sunscreen compounds alone, or employing both of said sunscreen compounds, but in ratios without those values indicated below.

Briefly, the present invention features novel photoprotective/cosmetic compositions comprising, in a cosmetically acceptable vehicle, diluent or carrier, (i) an effective amount of benzene-1,4-di(3-methylidene-10-camphorsulfonic)acid, or, optionally, the partially or totally neutralized deivatives thereof, as a first sunscreen compound, and (ii) an effective amount of 2-ethylhexyl α-cyano-β,β-diphenylacrylate, as a second sunscreen compound, the compounds (i) and (ii) being present in synergistically effective proportions.

The present invention also features the use of such compositions as, or for the formulation of, sunscreen/cosmetic compositions intended for the photoprotection of the skin and/or the hair against ultraviolet irradiation, in particular solar radiation.

The cosmetic treatment for the photoprotection of the skin and/or the hair against ultraviolet irradiation, in particular solar radiation, comprises topically applying thereto an effective amount of a sunscreen/cosmetic composition as described above.

DETAILED DESCRIPTION OF BEST MODE AND PREFERRED EMBODIMENTS OF THE INVENTION

More particularly according to the present invention, benzene-1,4-di(3-methylidene-10-camphorsulfonic)acid and the various salts thereof (compound A), which are described especially in FR-A-2,528,420 and FR-A-2,693,347, are sunscreen compounds that are per se known to this art (so-called broad-band screening compounds) and which absorb ultraviolet rays of wavelengths ranging from 280 to 400 nm, with absorption maxima from 320 to 400 nm, in particular at about 345 nm. These screening compounds have the following structural formula (I):

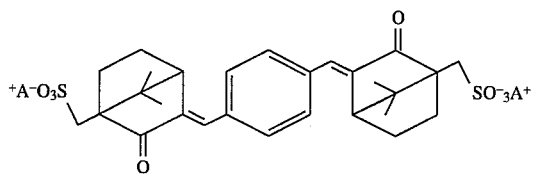

(I)

in which A is a hydrogen atom, an alkali metal or, alternatively, a radical $NH(R)_3^+$, wherein the radicals R, which may be identical or different, are each a hydrogen atom, a $C_1$–$C_4$ alkyl or hydroxyalkyl radical or, alternatively, a group $M^{n+}/n$, wherein $M^{n+}$ is a polyvalent metal cation in which n is equal to 2, 3 or 4, $M^{n+}$ preferably being a metal cation selected from among $Ca^{2+}$, $Zn^{2+}$, $Mg^{2+}$, $Ba^{2+}$, $Al^{3+}$ and $Zr^{4+}$. It should be appreciated that the above compounds of formula (I) may exist as "cis-trans" isomers about one or more double bond(s) and that all such isomers are within the scope of the present invention.

Similarly, 2-ethylhexyl α-cyano-β,β-diphenylacrylate (compound B), also referred to as octocrylene, is a liquid lipophilic sunscreen compound that is also per se known to this art for its activity in the UV-B range. This too is a commercially available compound, marketed under the trademark "UVINUL N 539" by BASF. It has the following structural formula (II):

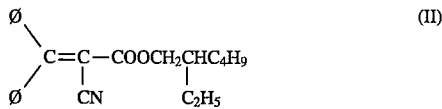

(II)

in which φ is a phenyl radical.

The compound A is advantageously present in the compositions according to the invention at a concentration ranging from 0.2% to 10% by weight relative to the total weight of the composition, and compound B is advantageously present at a concentration ranging from 0.5% to 20% by weight, also relative to the total weight of the composition. The overall content of the mixture of compound A and compound B preferably does not exceed 25% of the total weight of the final composition.

From a practical standpoint, the aforesaid two compounds A and B are preferably both present in the final composition in the respective proportions such that the synergy is optimal, as regards the protection factor imparted by the resulting association. The exact range of the [compound B/compound A] weight ratios in which this optimal synergy is actually attained may vary slightly depending on the total amount of sunscreen compounds A and B used, in particular whether the compound A is an acid or salt. Advantageously, this ratio ranges from about 0.25 to 8, more preferably from 0.5 to 7 and even more preferably from 1 to 5.

Moreover, the concentrations and ratios of compounds A and B are typically selected such that the sun protection factor of the final composition is preferably at least 2.

In a preferred embodiment of the present invention, the cosmetically acceptable vehicle, diluent, carrier or support in which the various compounds A and B are formulated is an emulsion of oil-in-water type.

Of course, the sunscreen/cosmetic compositions according to the invention may contain one or more additional hydrophilic or lipophilic sunscreen agents active in the UV-A and/or UV-B range (absorbers), other than the two sunscreen compounds indicated above. Exemplary of such additional sunscreens are cinnamic derivatives, salicylic derivatives, camphor derivatives, triazine derivatives, benzophenone derivatives, dibenzoylmethane derivatives, β,β-diphenylacrylate derivatives, p-aminobenzoic acid derivatives, and the sunscreen polymers and sunscreen silicones described in WO-93/04,665. Other examples of organic sunscreen agents are described in EO-A-0,487,404.

The compositions according to the invention may also contain agents for the artificial tanning and/or browning of the skin (self-tanning agents) such as, for example, dihydroxyacetone (DHA).

The cosmetic compositions according to the invention may also contain pigments or, alternatively, nanopigments (average size of the primary particles: generally ranging from 5 nm to 100 nm, preferably from 10 to 50 nm) of coated or uncoated metal oxides such as, for example, nanopigments of titanium dioxide (amorphous or crystallized in rutile and/or anatase form), of iron oxide, of zinc oxide, of zirconium oxide or of cerium oxide, which are all photoprotective agents that are per se well known to this art and which are effective by physical blocking (reflection and/or diffusion) of the UV irradiation. Conventional coating agents include, moreover, alumina and/or aluminum stearate. Such coated or uncoated metal oxide nanopigments are described, in particular, in EP-A-0,518,772 and EP-A-0,518,773.

The compositions of the invention may additionally comprise conventional cosmetic additives and adjuvants selected especially from among fats, organic solvents, ionic or nonionic thickening agents, softeners, antioxidants and especially anti-free-radical antioxidants, opacifying agents, stabilizing agents, emollients, silicones, α-hydroxy acids, anti-foaming agents, hydrating agents, vitamins, fragrances, preservatives, surfactants, fillers, insect repellants, sequestering agents, polymers, propellants, basifying or acidifying agents, dyes and colorants, or any other ingredient usually employed in cosmetics, in particular for the production of sunscreen/cosmetic compositions in emulsion form.

The fats may comprise an oil or a wax or mixtures thereof, and may also comprise fatty acids, fatty alcohols and fatty acid esters. The oils may be selected from among animal, plant, mineral or synthetic oils and, especially, from among liquid petrolatum, paraffin oil, volatile or non-volatile silicone oils, isoparaffins, poly-α-olefins, fluoro oils and perfluoro oils. Similarly, the waxes may be selected from among animal, fossil, plant, mineral or synthetic waxes that are per se known to this art.

Exemplary organic solvents include the lower polyols and alcohols.

The thickening agents may be selected, especially, from among crosslinked polyacrylic acids, modified or unmodified guar gums and celluloses such as hydroxypropyl guar gum, methylhydroxyethylcellulose and hydroxypropylmethylcellulose.

The aforesaid optional additional sunscreen compounds, adjuvants and additives, and/or the respective amounts thereof, are selected such that the synergistic effect of the basic binary immixture (in respect of the protection factors) is not adversely affected, or is not substantially adversely affected.

In this respect, it will be appreciated that a sunscreen emulsion comprising, as the active photoprotective agents thereof, a ternary combination comprising 2% of benzene-1,4-di(3-methylidene-10-camphorsulfonic)acid, 6% of 2-ethylhexyl α-cyano-β,β-diphenylacrylate ("UVINUL N 539") and 2% of 4-tert-butyl-4'-methoxydibenzoylmethane ("Parsol 1789") is described in EP-A-518,772 (Example 3). However, as will be seen from the examples below, the presence of the Parsol 1789 completely inhibits the synergistic effect which would normally be elicited by the binary sunscreen combination if it were used alone.

The compositions of the invention may be formulated according to techniques well known to this art, in particular those intended for the preparation of emulsions of oil-in-water or water-in-oil type.

The subject compositions may, in particular, be in simple or complex (O/W, W/O, O/W/O or W/O/W) emulsion form such as a cream, a milk, a gel, an ointment or a cream gel, in powder form or in solid stick form and may optionally be packaged as an aerosol and may be provided in the form of a foam or a spray.

When it is an emulsion, the aqueous phase of this emulsion may comprise a nonionic vesicle dispersion prepared according to known processes (Bangham, Standish and Watkins, *J. Mol. Biol*, 13, 238 (1965), FR-2,315,991 and FR-2,416,008).

The cosmetic compositions of the invention are useful for protecting the human epidermis or the hair against the damaging effects of ultraviolet rays, as sunscreen compositions or as makeup products.

When the cosmetic compositions according to the invention are used for photoprotection of the human epidermis against UV rays, or as sunscreen compositions, they may be formulated as a suspension or a dispersion in solvents or fats, in the form of a nonionic vesicle dispersion or, alternatively, in the form of an emulsion, preferably of oil-in-water type, such as a cream or a milk, or in ointment, gel, cream gel, solid stick, stick, aerosol foam or spray form.

When the cosmetic compositions according to the invention are used for the photoprotection of the hair, they may be formulated as a shampoo, a lotion, a gel, an emulsion, a nonionic vesicle dispersion or a lacquer for the hair and may constitute, for example, a composition to be rinsed, to be applied before or after shampooing, before or after dyeing or bleaching, before, during or after permanent-waving or hair-straightening, a styling or treating lotion or gel, a blow-drying or hair-setting lotion or gel, or a composition for the permanent-waving or straightening, dyeing or bleaching of the hair.

When the subject compositions are used as a makeup product for the eyelashes, the eyebrows or the skin, such as an epidermal treatment cream, a foundation, a lipstick, an eyeshadow, a blush, a mascara or "eyeliner", they may be in anhydrous or aqueous, solid or pasty form, such as oil-in-water or water-in-oil emulsions, nonionic vesicle dispersions or, alternatively, suspensions.

For example, for the photoprotective/sunscreen formulations in accordance with this invention which comprise a vehicle of oil-in-water emulsion type, the aqueous phase (comprising hydrophilic sunscreen agents in particular) generally constitutes from 50% to 95% by weight, preferably from 70% to 90% by weight, relative to the total formulation, the oily phase (comprising lipophilic sunscreen agents in particular) from 5% to 50% by weight, preferably from 10% to 30% by weight, relative to the total formulation, and the (co)emulsifying agent(s) from 0.5% to 20% by weight, preferably from 2% to 10% by weight, relative to the total formulation.

The cosmetic treatment of the skin or hair to protect same against the deleterious effects of UV rays, especially those contained in solar radiation, comprises applying thereto an effective amount of a sunscreen/cosmetic composition as described above.

In order to further illustrate the present invention and the advantages thereof, the following specific examples are given, it being understood that same are intended only as illustrative and in nowise limitative.

EXAMPLE 1

A variety of photoprotective/sunscreen formulations were prepared, in the form of an emulsion of oil-in-water type and which contained (the amounts are expressed in weight % with respect to the total weight of the composition):

| | |
|---|---|
| (a) a first photoprotective/sunscreen agent A which was benzene-1,4-di(3-methylidene-10-camphorsulfonic)acid, in a proportion of | x % |
| (b) a second photoprotective/sunscreen agent B which was 2-ethylhexyl α-cyano-β,β-diphenylacrylate ("UVINUL N 539"), in a proportion of | y % |
| (c) Mixture of cetylstearyl alcohol and of cetylstearyl alcohol oxyethylenated with 33 moles of ethylene oxide, marketed under the trademark "SINNOWAX AO" by Henkel (emulsifier) | 7% |
| (d) Mixture of glyceryl mono-, di- and tristearate (coemulsifier)) | 2% |
| (e) Triglycerides of $C_8$–$C_{12}$ fatty acids ("MIGLYOL 812") | 2% |
| (f) Polydimethylsiloxane | 1.5% |
| (g) Cetyl alcohol | 1.5% |
| (h) Water | qs 100% |

These formulations (numbered 1 and 2 for those in accordance with the invention) had different y/x ratios by weight of the photoprotective/sunscreen agent B to the photoprotective/sunscreen agent A. In addition, for each of these formulations, comparative corresponding formulations were prepared, either containing only the photoprotective/sunscreen agent A at the x+y concentration by weight, or only containing the photoprotective/sunscreen agent B, also at the x+y concentration by weight, or containing the photoprotective/sunscreen agents A and B, still at the overall x+y concentrations by weight, but in proportions not in accordance with the invention.

Each of these emulsions was prepared by dissolving the photoprotective/sunscreen agents in the fatty phase, then adding the (co)emulsifiers to this fatty phase, heated to approximately 80° C., and, lastly, adding, with rapid stirring, the water which had been heated beforehand to the same temperature.

For each of the formulations thus prepared, the sun protection factor (SPF) which was associated therewith was then determined. Measurement of the protection factor was carried out according to the following technique (in vitro): these formulations were applied, in a proportion of 2 mg of product/cm² of skin, to the back of 5 human models and the protected skin regions and the unprotected skin regions were then subjected, simultaneously, to the action of a sunlight simulator marketed under the trademark "Xénon Müller WG 305-1 mm"; the sun protection factor (SPF) was then calculated mathematically by the ratio of the irradiation time which was required to attain the erythematogenic threshold with the UV screening agent (protected region) to the time which was necessary to attain the erythematogenic threshold without a UV screening agent (unprotected region).

The compositions of the various formulations examined and the results obtained, as a mean protection factor (mean over the 5 models), are reported in Table I below:

TABLE 1

| Sunscreen agents | Formulations | | | | | | |
|---|---|---|---|---|---|---|---|
| | 1 | 1A | 1B | 2 | 2A | 2B | 2C |
| A (x %) | 4 | 14 | — | 2.6 | 9 | — | 1 |
| B (y %) | 10 | — | 14 | 6.4 | — | 9 | 8 |

TABLE 1-continued

| Sunscreen agents | Formulations | | | | | | |
|---|---|---|---|---|---|---|---|
| | 1 | 1A | 1B | 2 | 2A | 2B | 2C |
| A + B (x + y %) | 14 | 14 | 14 | 9 | 9 | 9 | 9 |
| Ratio by weight y/x | 2.5 | — | — | 2.5 | — | — | 8 |
| Mean SPF (standard deviation) | 29.8 (5.8) | 13.5 (3.5) | 12.8 (3.8) | 20.3 (1.8) | 9.4 (1.5) | 8.45 (2.45) | 10.7 (1.3) |

These results clearly demonstrate the marked synergistic effect obtained with the compositions 1 and 2 in accordance with the invention.

EXAMPLE 2

Four photoprotective/sunscreen formulations (I, II, III and IV) were prepared, in the form of an emulsion of oil-in-water type and which contained (the amounts are expressed in weight % with respect to the total weight of the composition):

| | |
|---|---|
| (a) a first photoprotective/sunscreen agent A which was benzene-1,4-di(3-methylidene-10-camphorsulfonic) acid, in a proportion of | x % |
| (b) a second photoprotective/sunscreen agent B which was 2-ethylhexyl α-cyano-β,β-diphenylacrylate ("UVINUL N 539"), in a proportion of | y % |
| (c) a third photoprotective/sunscreen agent C was 4-tert-butyl-4'-methoxydibenzoylmethane ("PARSOL 1789"), in a proportion of | z % |
| (d) Mixture of glyceryl monostearate and the stearate of polyethylene glycol containing 100 mol of ethylene oxide, marketed under the trademark ("ARLACEL 165") (emulsifier) | 1.5% |
| (e) Mixture of benzoates of $C_{12}/C_{15}$ alcohols ("FINSOLV TN") | 4% |
| (f) Moisturizers | 15% |
| (g) Crosslinked polyacrylic acid | 0.2% |
| (h) Potassium hexadecyl phosphate | 1% |
| (i) Cetyl alcohol | 1.5% |
| (j) Stearic acid | 1.5% |
| (k) Triethanolamine | 2.7% |
| (l) Preservatives, antioxidants, sequestering agents | qs |
| (m) Water | qs 100% |

The sun protection factor (SPF) attributed to each of these formulations was then measured according to the procedure indicated in Example 1.

The compositions of the various formulations examined and the results obtained, as a mean protection factor (mean over the 5 models), are reported in the Table II below:

TABLE II

| Sunscreen agents | Formulations | | | |
|---|---|---|---|---|
| | I | II | III | IV |
| A (x %) | 4 | 0 | 0 | 4 |
| B (y %) | 0 | 10 | 0 | 10 |
| C (z %) | 0 | 0 | 2 | 2 |

TABLE II-continued

| Sunscreen agents | Formulations | | | |
|---|---|---|---|---|
| | I | II | III | IV |
| Mean SPF (standard deviation) | 5.8 (3.1) | 7.9 (1.4) | 2.8 (0.7) | 17.9 (4.9) |

It will be appreciated that the sun protection factor associated with the composition IV (equal to 17.9) was not significantly greater, taking account of the standard deviations, than the simple arithmetic sum (equal to 16.5) of the sun protection factors associated with the compositions A, B and C which contained only a single screening agent.

This example thus evidences that the synergistic effect attributed to the binary photoprotective/sunscreen combination in accordance with the invention was destroyed in the presence of a third photoprotective/sunscreen agent of Parsol 1789 type.

EXAMPLE 3

A specific example of a photoprotective/sunscreen composition in accordance with the invention, in the form of an alcoholic gel, is as follows:

| | |
|---|---|
| (a) Benzene-1,4-di(3-methylidene-10-camphorsulfonic) acid | 1.5 g |
| (b) 2-Ethylhexyl α-cyano-β,β-diphenylacrylate ("UVINUL N 539") | 5 g |
| (c) 96% Ethyl alcohol | 50 g |
| (d) Hydroxypropyl ether of cellulose (MW = 300,000) | 1 g |
| (e) Diisopropyl adipate | 4 g |
| (f) Glycerol | 4 g |
| (g) Preservatives | qs |
| (h) Fragrances | qs |
| (i) "SILICONE DC 245 FLUID" marketed by Dow Corning | qs 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition adopted for the photoprotection of human skin and/or hair, comprising a photoprotecting synergistically effective amount of (i) benzene-1,4-di(3-methylidene-10-camphorsulfonic)acid, optionally either partially or totally neutralized, and (ii) 2-ethylhexyl α-cyano,β,β-diphenylacrylate, in a cosmetically acceptable vehicle, diluent or carrier therefor, wherein said composition optionally contains additional sunscreen compounds, adjuvants and/or additives, with the proviso that if such additional sunscreen compounds, adjuvants and/or additives are present, that said additional compounds do not substantially adversely affect the synergistic photoprotection achieved by the combination of said sulfonic acid compound (i) and said diphenylacrylate compound (ii).

2. The sunscreen/cosmetic composition as defined by claim 1, comprising from 0.2% to 10% by weight of said sulfonic acid compound (i).

3. The sunscreen/cosmetic composition as defined by claim 2, comprising from 0.5% to 20% by weight of said diphenylacrylate compound (ii).

4. The sunscreen/cosmetic composition as defined by claim 1, wherein the ratio by weight of said diphenylacrylate compound (ii) to said sulfonic acid compound (i) ranges from 0.25 to 8.

5. The sunscreen/cosmetic composition as defined by claim 4, said ratio by weight ranging from 0.5 to 7.

6. The sunscreen/cosmetic composition as defined by claim 5, said ratio by weight ranging from 1 to 5.

7. The sunscreen/cosmetic composition as defined by claim 1, comprising an oil-in-water emulsion.

8. The sunscreen/cosmetic composition as defined by claim 1, comprising a water-in-oil emulsion.

9. The sunscreen/cosmetic composition as defined by claim 1, further comprising at least one additional hydrophilic or lipophilic organic UV-A and/or UV-B sunscreen.

10. The sunscreen/cosmetic composition as defined by claim 9, further comprising at least one cinnamic derivative, salicylic derivative, camphor derivative, triazine derivative, benzophenone derivative, dibenzoylmethane derivative, β,β-diphenylacrylate derivative, p-aminobenzoic acid derivative, sunscreen polymer, or sunscreen silicone.

11. The sunscreen/cosmetic composition as defined by claim 1, further comprising a photoprotecting effective amount of particulates of at least one inorganic pigment or nanopigment.

12. The sunscreen/cosmetic composition as defined by claim 11, said at least one pigment or nanopigment comprising titanium dioxide, zinc oxide, iron oxide, zirconium oxide, cerium oxide, or mixture thereof.

13. The sunscreen/cosmetic composition as defined by claim 1, further comprising at least one active agent for the artificial tanning and/or browning of human skin.

14. The sunscreen/cosmetic composition as defined by claim 1, further comprising at least one cosmetically acceptable adjuvant or additive.

15. The sunscreen/cosmetic composition as defined by claim 14, said at least one adjuvant or additive comprising a fat, organic solvent, ionic or nonionic thickening agent, softener, antioxidant, anti-free-radical antioxidant, opacifying agent, stabilizing agent, emollient, silicone, α-hydroxy acid, anti-foaming agent, hydrating agent, vitamin, fragrance, preservative, surfactant, filler, sequestering agent, polymer, propellant, insect repellent, basifying or acidifying agent, dye, colorant, or mixture thereof.

16. The sunscreen/cosmetic composition as defined by claim 1, comprising a nonionic vesicle dispersion, emulsion, cream, milk, gel, cream gel, ointment, suspension, dispersion, powder, solid stick, foam or spray.

17. The sunscreen/cosmetic composition as defined by claim 1, comprising a makeup.

18. The sunscreen/cosmetic composition as defined by claim 17, comprising an anhydrous or aqueous solid or paste, emulsion, suspension, or dispersion.

19. The sunscreen/cosmetic composition as defined by claim 1, comprising a shampoo, lotion, gel, emulsion, nonionic vesicle dispersion, hair lacquer, or rinse.

20. The sunscreen/cosmetic composition as defined by claim 1, having a sun protection factor of at least 2.

21. The sunscreen/cosmetic composition as defined by claim 1, said sulfonic acid compound (i) having the structural formula (I):

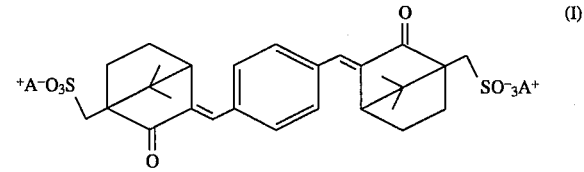

in which A is a hydrogen atom, an alkali metal or a radical $NH(R)_3^+$, wherein the radicals R which may be identical or different, are each a hydrogen atom or a $C_1$–$C_4$ hydroxyalkyl or alkyl radical, or a group $M^{n+}$, wherein $M^{n+}$ is a polyvalent metal cation in which n is equal to 2, 3 or 4.

22. A method for protecting human skin and/or hair against the deleterious effects of ultraviolet irradiation, comprising topically applying thereto an effective amount of the sunscreen/cosmetic composition as defined by claim 1.

23. A method for protecting human skin and/or hair against the deleterious effects of solar radiation, comprising topically applying thereto an effective amount of the sunscreen/cosmetic composition as defined by claim 1.

24. The topically applicable sunscreen/cosmetic composition of claim 1 which does not contain any sunscreen compounds which adversely affect the synergistic photoprotection achieved by the combination of said (i) sulfonic acid compound, and said (ii) diphenylacrylate compound.

25. The topically applicable sunscreen/cosmetic composition of claim 24 which does not contain 4-tert-butyl-yl-4-methoxydibenzoyl-methane.

* * * * *